(12) United States Patent
Mann

(10) Patent No.: US 6,736,974 B1
(45) Date of Patent: May 18, 2004

(54) CHROMATOGRAPHY COLUMN AND METHOD OF OPERATION

(75) Inventor: Herbert Mann, Chattanooga, TN (US)

(73) Assignee: Mann Welding Company, Chattanooga, TN (US)

( * ) Notice: Subject to any disclaimer, the term of this patent is extended or adjusted under 35 U.S.C. 154(b) by 0 days.

(21) Appl. No.: 10/016,231

(22) Filed: Nov. 2, 2001

(51) Int. Cl.⁷ .............................................. B01D 15/08
(52) U.S. Cl. .................................... 210/656; 210/198.2
(58) Field of Search .............................. 210/635, 656, 210/659, 198.2; 95/82; 96/101

(56) References Cited

U.S. PATENT DOCUMENTS

| | | | |
|---|---|---|---|
| 4,470,910 A | * 9/1984 | Quemerais | 210/656 |
| 4,597,866 A | * 7/1986 | Couillard | 210/198.2 |
| 4,769,141 A | * 9/1988 | Couillard | 210/198.2 |
| 4,861,473 A | * 8/1989 | Shackelford | 210/198.2 |
| 4,891,133 A | * 1/1990 | Colvin | 210/198.2 |
| 5,021,162 A | * 6/1991 | Sakamoto | 210/635 |
| 5,141,635 A | * 8/1992 | LePlang | 210/198.2 |
| 5,167,809 A | * 12/1992 | Mann | 210/198.2 |
| 5,169,522 A | * 12/1992 | Shalon | 210/198.2 |
| 5,213,683 A | * 5/1993 | Mann | 210/198.2 |
| 5,282,973 A | * 2/1994 | Mann | 210/656 |
| 5,423,982 A | * 6/1995 | Jungbauer | 210/198.2 |
| 5,462,659 A | * 10/1995 | Saxena | 210/198.2 |
| 5,486,289 A | * 1/1996 | McCullough | 210/198.2 |
| 5,667,675 A | * 9/1997 | Hatch | 210/198.2 |
| 5,866,008 A | * 2/1999 | Shalon | 210/656 |
| 5,902,485 A | * 5/1999 | Davis | 210/656 |
| 5,919,361 A | * 7/1999 | Moran | 210/198.2 |
| 5,951,873 A | * 9/1999 | Shalon | 210/656 |
| 6,001,260 A | * 12/1999 | Hatch | 210/656 |
| 6,190,560 B1 | * 2/2001 | Mann | 210/656 |

* cited by examiner

*Primary Examiner*—Ernest G. Therkorn
(74) *Attorney, Agent, or Firm*—Stephen J. Stark; Miller & Martin LLP

(57) ABSTRACT

A chromatography column has valve and method for filling it with a slurry of media, the valve utilizing a piston to compact the slurry in the column. The piston moves through a cavity in communication with both a slurry inlet and slurry ports which are in communication with the interior of the chromatography column. The piston assists in compacting the slurry within the column. The method of filling the column does not require disassembly of the column. The piston may also be utilized to change the valve position from a slurry fill position to a normal operation position or other position.

11 Claims, 5 Drawing Sheets

CHROMATOGRAPHY COLUMN AND METHOD OF OPERATION

BACKGROUND OF THE INVENTION

1. Field of the Invention

The present invention relates an apparatus and method of operating a chromatography column and, more particularly, to such a chromatography column and the method for performing maintenance, such as changing resin retention screens within the chromatography column without requiring the use of a crane to disassemble the column.

2. Description of Related Art

Chromatography is a process of separating the components of a mixture of chemical substances through the percolation of fluid through a body or bed of comminuted or porous rigid material, known as media. In the process, the various component are often resolved, or separated, by their selective retardation as they are transported through the bed by a moving fluid or buffer. A solution of the substances to be separated becomes the moving phase of the system passing through the interstices in the stationary or continuous phase which are finely divided particles, possibly in the form of a gel slurry.

The substances in the moving phase are poured into the top of a chromatography column filled with the finely divided material, i.e., the media, that can absorb differentially the substances to be separated. The particular material used for the media varies widely with the substances to be separated. As the solution percolates down the column the components are separated from the buffer fluid which generally is pumped back into the top of the column so as to again pass down through the bed as a carrier. The different substances as they travel down the column at different rates form bands of the different substances which are individually collected at the outlet.

A chromatography column typically comprises a hollow vertically disposed cylindrical housing including a liquid dispensing section at the upper end and through which the buffer and substances to be separated are dispensed to the media bed, and a liquid collecting section at the lower end for collecting the substances and buffer individually. The media or bed through which the buffer fluid and mixture to be separated and purified percolates is located between these sections. The liquid dispensing section and liquid collecting section may each include a respective distribution plate and at least one of the plates may be connected in an assembly with an axially movable plunger-like body positioned within the housing. After the column is charged with the bed media, the plunger body may be forced toward the bottom to compress or pressurize the media bed which has been poured into the column. Alternatively, a fixed bed media may compress the media bed.

Chromatography columns typically require periodic maintenance and inspection within the column. Prior art designs have allowed for the plunger to be moved with hydraulics to about two inches or less above the top of the cylinder to allow visual inspection within the column. No prior art designs are known to exist which allowed the plunger to be lifted high enough to perform maintenance on the interior portion of the plunger or within the cylinder. Such maintenance includes the replacement of a resin retention screen which normally allows fluid to flow through orifices typically on the order of about ten microns while preventing resin from leaving the column. The screens are held to the plunger with connectors and an inner clamp nut.

In the prior art, the plunger had to be completely removed from the cylinder with a crane in order to replace the screen and/or work on the distributor plate since the plunger could only be lifted about two inches or less above the cylinder which did not provide enough clearance for a mechanic to access the connectors or inner clamp nut to disconnect and replace the screen.

A second screen and plate is typically located at the bottom of the cylinder on a base. In many circumstances, the bottom of the cylinder assists in holding the screen in place against the base so that it cannot be removed from within the cylinder upwards without first removing the cylinder relative to the base. Additionally connectors and an inner clamp nut also assist in retaining the bottom screen in place. In the prior art, the cylinder had to be disconnected from the bottom and lifted with a crane from the bottom. The bottom screen could then be replaced in a similar fashion as the top screen.

Many chromatography columns are located in clean rooms. Often the solutions utilized may be highly flammable, such as tolulene or acetate. Few cranes have been devised which can meet the requirements of a clean room. Additionally, the cost of a specially designed crane is believed to be very expensive. Furthermore, it is likely that the clean room would need to be designed around both the crane as well as the column for maintenance purposes. This would require higher ceilings and supports. Many column users avoid the problems of having a crane in a clean room by moving the columns from the clean room to another room for maintenance. Once the columns have been moved, they have to undergo a cleaning or verification procedure to be allowed back into the clean room. This is believed to be time consuming and tedious work.

Accordingly, a need exists to improve the maintenance methods by providing an improved chromatography column.

SUMMARY OF THE INVENTION

The present invention recognizes and addresses these needs and others.

Consequently, it is an object of the present invention to provide a chromatography column capable of lifting the plunger to a sufficient height above the cylinder to allow access to the lower surface of the plunger for maintenance.

It is another object of the present invention to provide a chromatography column capable of lifting the cylinder above the base to allow access to the bottom of the column, as well as access the bottom of the cylinder, in a preferred embodiment.

Accordingly, the present invention provides a chromatography column having a cylinder defining a cavity for containing media therein. A plunger, or piston, is operatively coupled to a hydraulic piston moveable through at least a portion of the cavity within the cylinder during operation. A base is normally connected to the cylinder. The plunger may be operatively coupled to the hydraulic piston to adjust the height of the plunger above the base to provide a desired resin height between the plunger and the base for operation. The plunger may also be utilized to exert a force on the resin to "pack" the resin in the column.

During maintenance, the plunger may be lifted with a drive system such as one including a first hydraulic piston. The plunger is lifted a distance sufficient to allow access to perform maintenance on the bottom surface of the piston, such as to replace a screen. This distance is preferably at least six inches and more preferably about twelve inches.

With the plunger in a raised position, safety rods may be positioned to ensure that the plunger will not drop should a hydraulic failure occur. After performing the maintenance, the safety rods may be removed, and the plunger lowered.

During a second maintenance procedure, the hydraulic system is configured to lift the cylinder by removing bolts which normally retain the cylinder against the base of the column. The hydraulic system may then lift the cylinder a second distance above the base to allow maintenance, such as replacement of a screen proximate to the base. Safety rods may be used between the cylinder and base during the maintenance. With the maintenance performed, the cylinder may be lowered and reconnected to the base.

The hydraulic system preferably includes a piston which is driven by a hydraulic cylinder. In the preferred embodiment, a plurality of hydraulic cylinders are utilized which are driven from a common hydraulic pressure source which is coupled to a controller. Upon receipt of a signal from a controller, the hydraulic cylinder(s) drive the hydraulic piston(s). Depending upon the configuration of the column, the piston(s) drive the plunger and/or the cylinder upwardly or downwardly.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENTS

Figure 1:
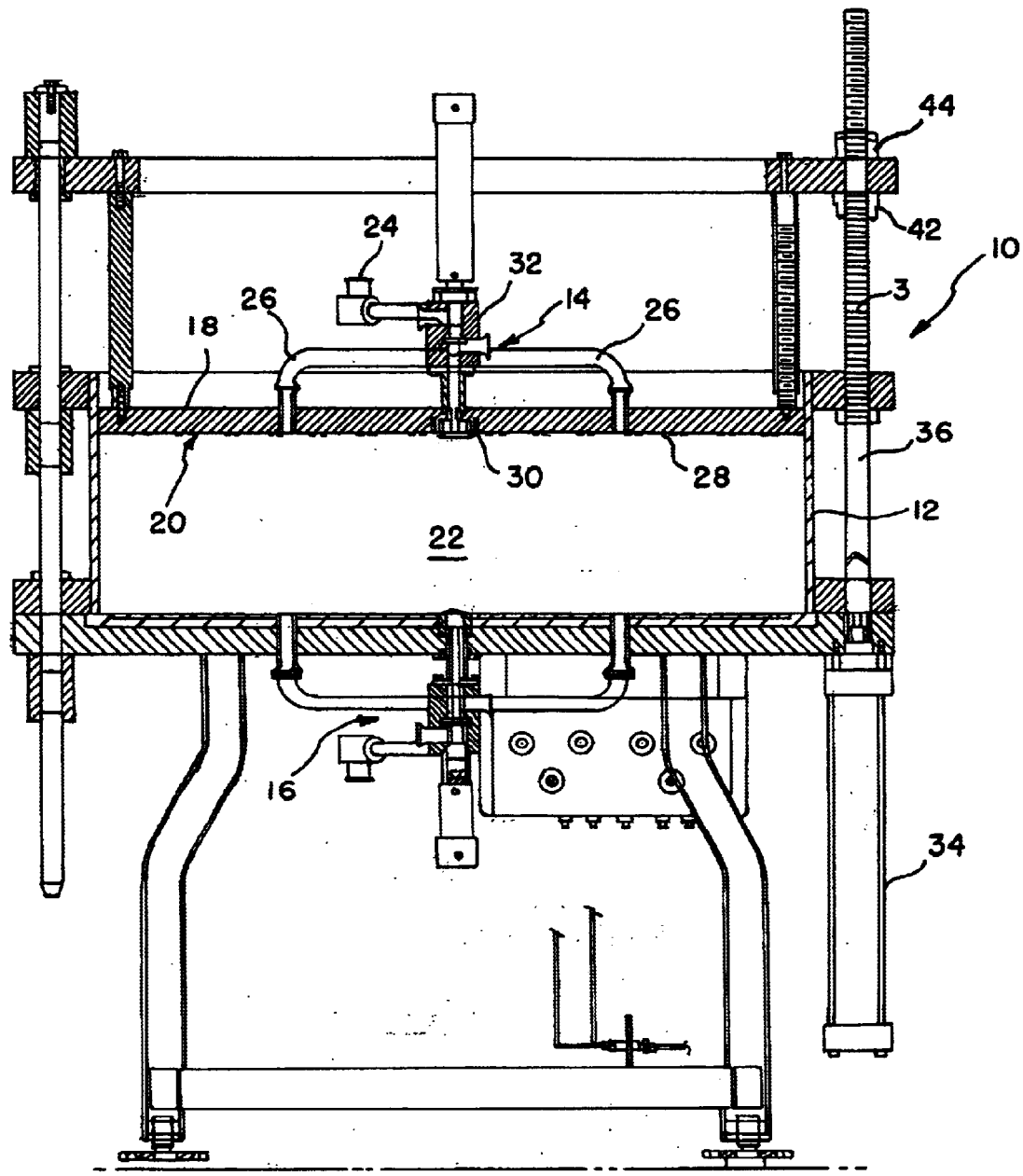
FIG. 1 is a side plan view of a chromatography column according to the present invention in a first operational position.

The present invention is concerned with a method and apparatus for permitting maintenance within a chromatography column which houses a slurry and/or media during operation. FIGS. 1–5 depict one such chromatography column 10 with the slurry removed. The column 10 comprises an elongated hollow cylindrical housing 12, or cylinder, having a dispersion section 14 at the top and a collecting section 16 at the bottom. The dispersion section 14 includes a cylindrical drum 18 having an upper cylindrical plunger head 20 formed at the lower end. The plunger 20 is normally disposed within the upper portion of the housing 12 such as illustrated in the first operational position of FIG. 1. The plunger 20 may also be moved, such as with a drive system similar to the hydraulic arrangement illustrated to the second operational position of FIG. 2. The movement of the head 20 allows for the compression of media to "pack" resin and/or for the use of a particularly sized media column with the cavity 22 formed between the dispersion and collection sections 14,16 and/or between the plunger 20 and the base 64.

The dispersion section 14 may also include a product inlet 24 along with an inlet manifold 26 to distribute incoming fluid throughout a top portion of a resin column contained within the cavity 22. An inlet screen 28 may be connected to the plunger head 20 by connectors such as TEFLON (TM) snaps (not illustrated) and/or an inner clamp nut 30. The distributor plate 31 may be removable as well. A discussion of a distributor plate 31 design may be found in U.S. Pat. No. 6,190,560. A slurry fill valve 32 such as the valve taught in co-owned U.S. Pat. No. 6,190,560 may also be connected to the plunger head 20 and/or dispersion section 14. The slurry fill valve 32 provides a way to fill the cavity 22 with resin without the need to lift the plunger 28 out of the cavity 22 within the cylinder 12. Although a preferred dispersion section 14 is described, other dispersion sections designs could be utilized as well.

Figure 2:
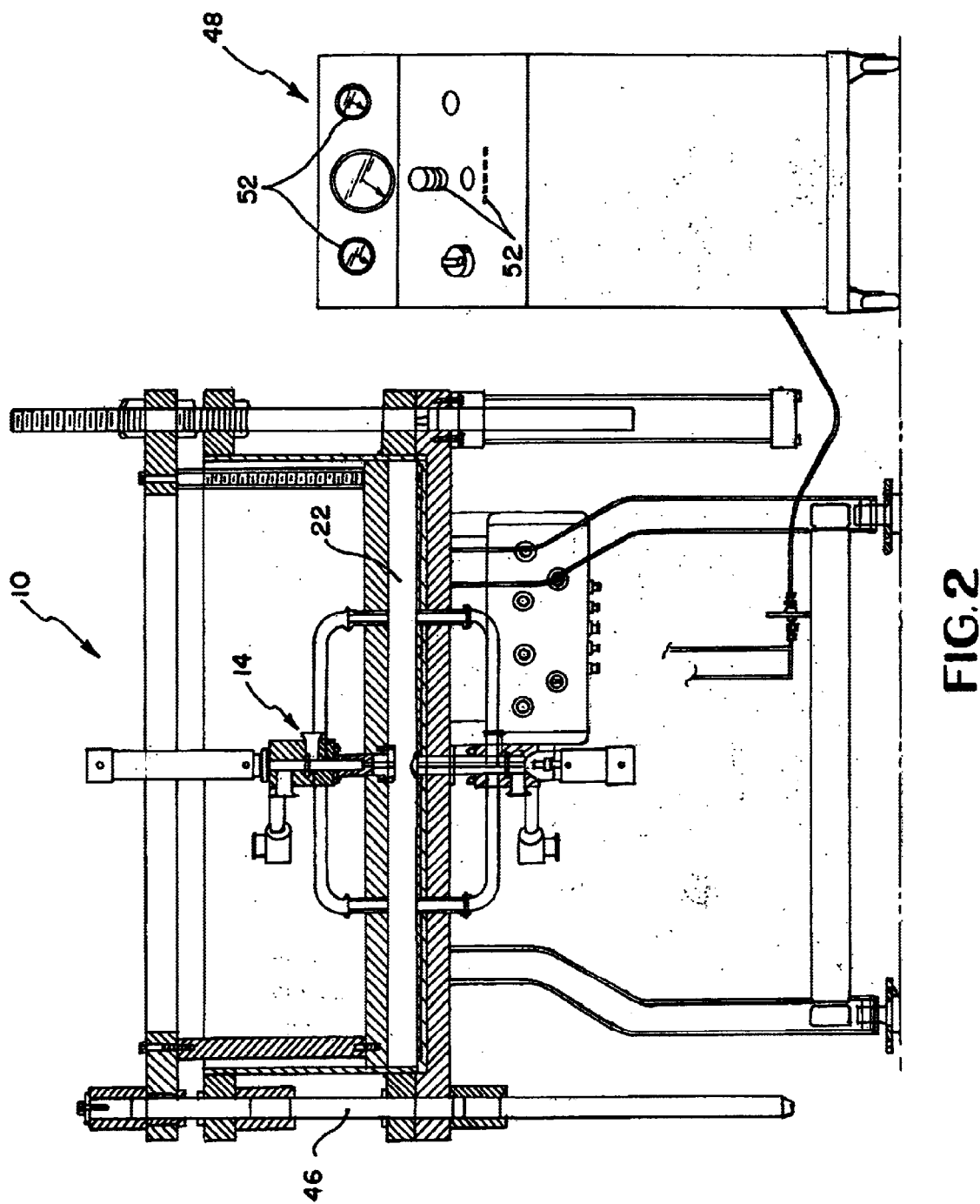
FIG. 2 is a side plan view of the chromatography column illustrated in FIG. 1 in a second operational position.

In order to move the plunger head 20 in an operational mode from the first operational position shown in FIG. 1 to the second operational position of FIG. 2, a drive system, illustrated as a hydraulic system is preferably utilized. Other systems, such as electric or pneumatic may be appropriate drive systems in other embodiments.

The drive system is comprised of at least one, and preferably three or more, drive cylinders 34. The drive cylinders 34 move drive pistons 36 which are coupled to the drum 18. In the preferred embodiment, a portion of the drive pistons is a threaded portion 38 to allow for the drive piston 36 to connect or couple to connection arms 40 at specific locations relative to the drive piston 36 such as with nuts 42,44. Guide rods 46 may be utilized in addition to the drive system to ensure linear movement of the drum 20 within the cavity 22 of the cylinder 12.

The drive system also includes a control unit 48 which may be operated to control movement of the plunger 20. The control unit may have a hydraulic engine which provides fluid under pressure to operate the drive cylinders 34 or may be connected to a hydraulic supply. Controls 50 allow an operator to direct the movement of the plunger 20 within the cylinder 12. Controls 50 may allow for operation of the hydraulic engine, or pump, a float switch, direction of movement selection and/or controlling valves. Gauges 52 allow for the operating parameters to be monitored. Gauges 52 may monitor air pressure, column pressure and/or drive system pressure, such as hydraulic pressure.

When intrusive maintenance is to be performed within the cavity of the cylinder 12 (which does not include visual inspection), the drive system 48 has been constructed to assist in this aspect, rather than needing a crane to lift components of the column 10 after substantial disassembly of the column 10. Intrusive maintenance is defined herein as needing more than two inches clearance between the top of the cylinder and the bottom of the plunger.

Figure 4:
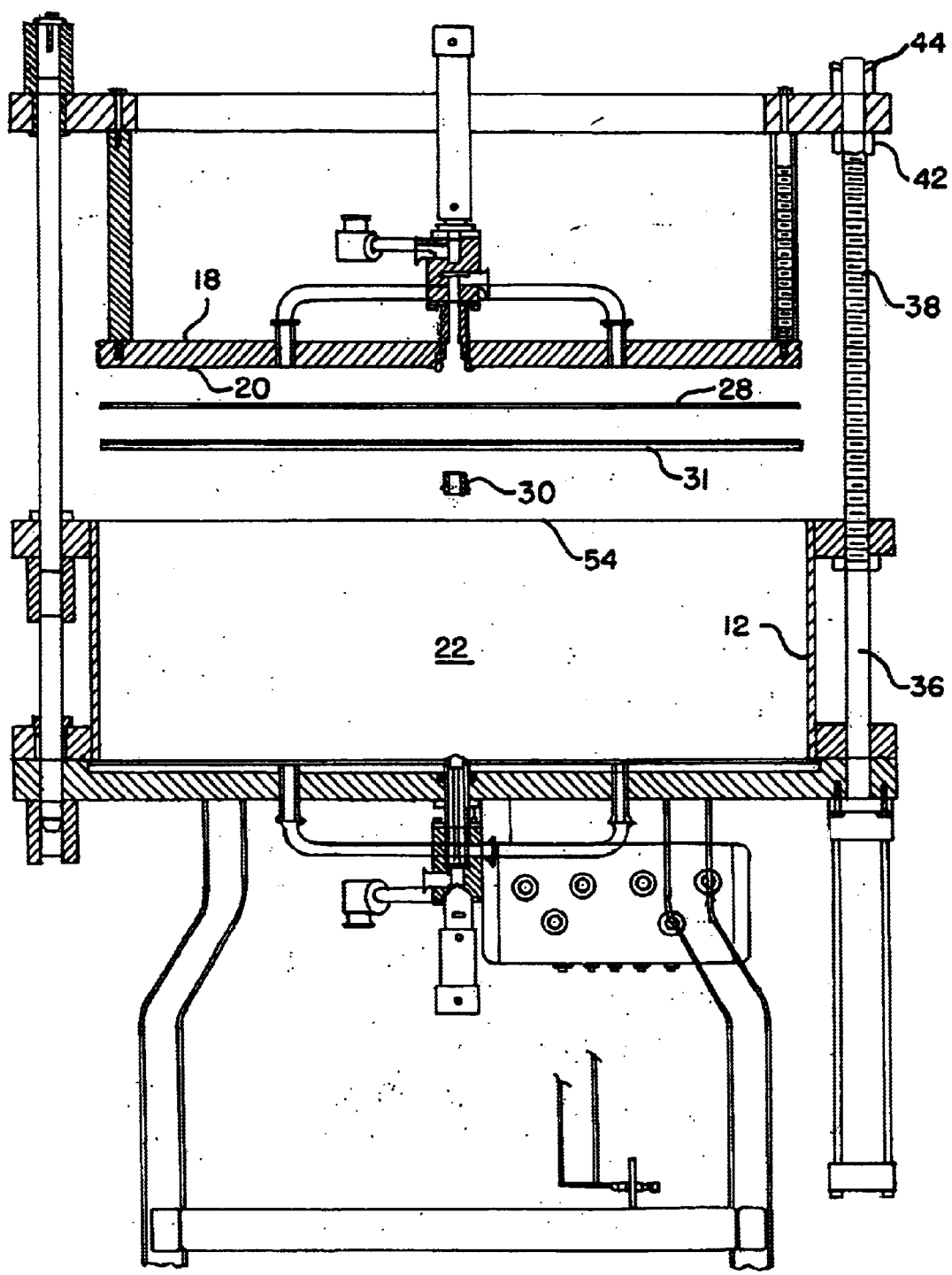
FIG. 4 is a side plan view of the chromatography column illustrated in FIG. 1 in a partially disassembled first maintenance position.

FIG. 4 shows a first maintenance position of the plunger 20 wherein the plunger 20 is raised a predetermined distance from a top 54 of the cavity 22 within the cylinder. The predetermined distance is greater than three inches, preferably greater than six inches, and most preferably about twelve inches. The predetermined distance is greater than the small distance allowed in the prior art designs which was intended for visual inspection of the interior of the column only. The predetermined distance may be accomplished through the use of a longer piston 36 than has been utilized in the prior art.

The use of the longer piston 36 to provide the predetermined distance which allows an operator to obtain access with a hand to the center of the drum 18 to access the nut 30 which was previously not possible. Furthermore, the distributor plate may be accessed as well. Accordingly, the method of raising the drum 18 for access to the plunger for a mechanic saves the expense and trouble associated with requiring a crane to lift the heavy drum 18 from the column 10. This saves space, cost, and reduces the time necessary to perform maintenance within the column 10. The nuts 42,44 may be repositioned about the threaded portion 38 as shown in FIG. 4 to allow the piston 36 to lift the plunger 20 as illustrated. Once the maintenance is complete, the plunger 20 may be lowered to return to an operational position and the nuts 42,44 reset to a proper operational configuration, if necessary.

Figure 5:
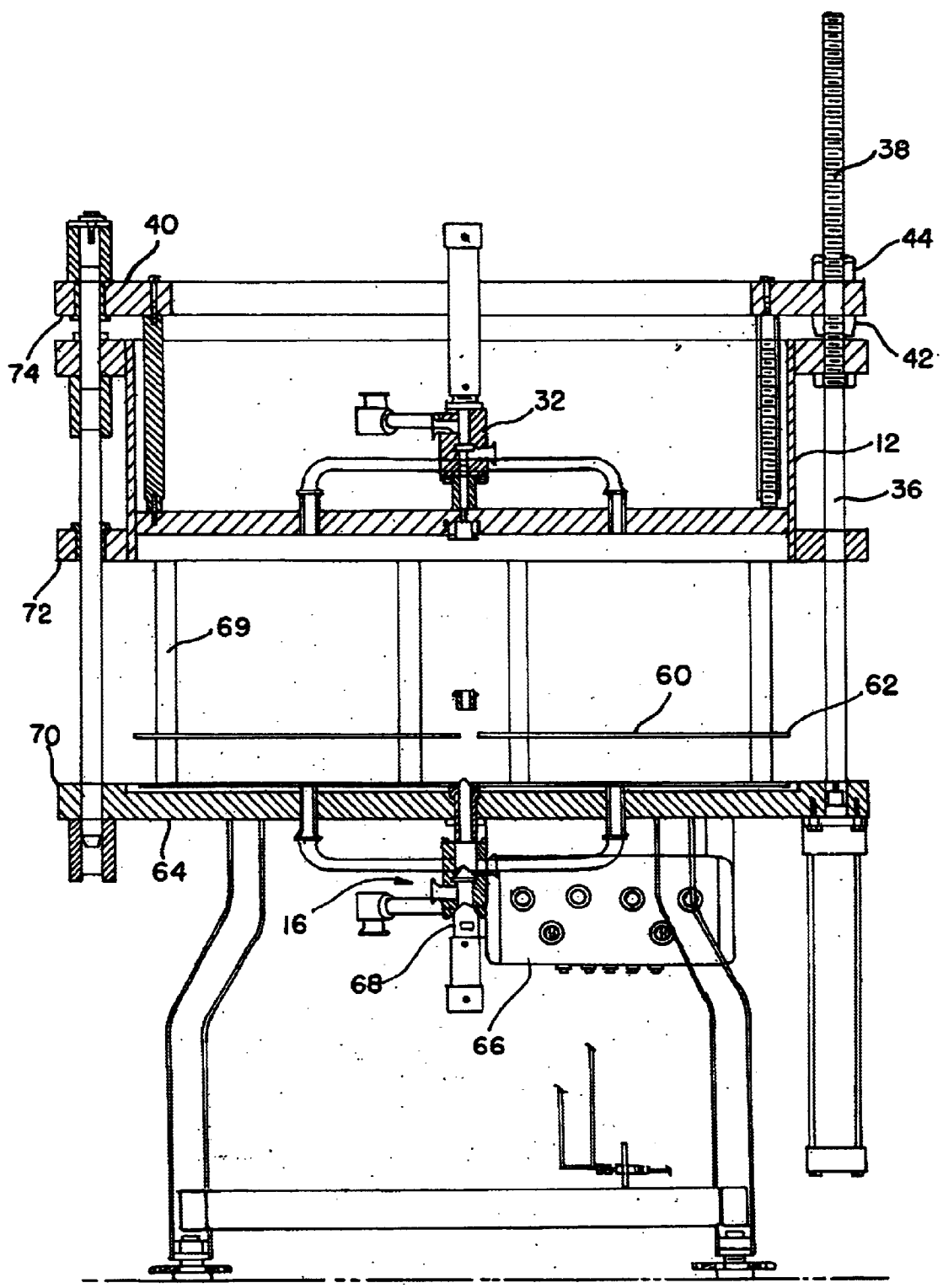
FIG. 5 is a side plan view of the chromatography column illustrated in FIG. 1 in a partially disassembled second maintenance position.

In order to perform a second maintenance operation, such as removal of the lower screen 60 which is typically positioned so that its outer edge 62 is between the cylinder 12 and the collecting section 16, the cylinder 12 may be raised by the drive system as illustrated in FIG. 5. The bolts 58 which normally secure the cylinder to the base 64 are removed, and the nut 42,44 may be coupled to the piston 36 to drive the cylinder 12 along with the drum 18 upwardly as illustrated. The collection section 16 may be substantially similar to the dispensing section 14 as illustrated, or it may be different in other embodiments. A controller 66 may be provided to control positions of the slurry fill valve 32 and the slurry outlet valve 68.

Figure 3:
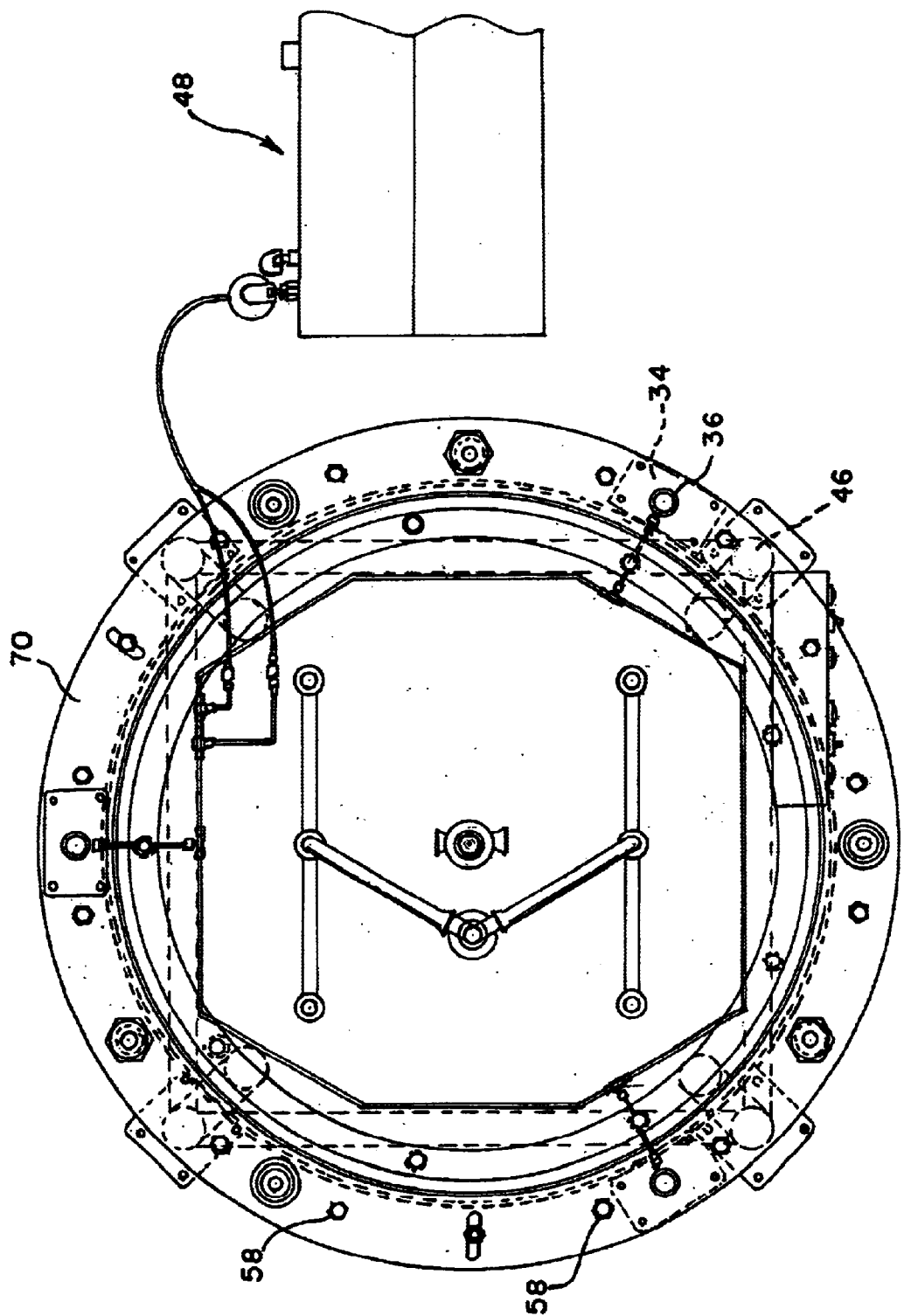
FIG. 3 is a bottom plan view, partly in cross section, of the chromatography column illustrated in FIG. 1.

Safety rods 69 may be inserted along portions of rim 70 illustrated in FIG. 3 to support the weight of the drum 18 and/or cylinder 12 during the maintenance operations so that hydraulic failure will not result in dropping of either of the plunger 20 and/or the cylinder 12. A safety rod could be similar to the guide rods 46 with retaining lips, possibly formed by nuts on threaded portions at the rims or lips 70,72,74 of the cylinder 12, base 64 and support arm 40 or may be separate members as illustrated. At least one guide rod 46, safety rod 69 and/or drive piston 36 may be removed to assist in installing support rods and/or removing screens 28,60.

The component parts, such as the drum 18, the cylinder 12, and the base are preferably constructed from stainless steel and/or high pickle alloy and/or acrylic. The drive system may be constructed out of appropriate materials including stainless steel. Three or more legs 76, only two of which are illustrated, are connected to the base 64. The drive cylinders 34 are connected to the rim 70 of the base.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A method of accessing the interior of a chromatography column comprising the steps of:
   a) providing a chromatography column having a dispersion section connected to a product inlet and a cylinder with a plunger connected to a drive system, said plunger moveable within a cavity of the cylinder in an operational mode, and a collecting section opposing the dispersion section;
   b) raising the plunger and dispersion section with the drive system a predetermined distance above a top of the cavity to a first maintenance position without the use of a crane;
   c) performing intrusive maintenance within the column without removing the plunger from the column;
   d) lowering the plunger and dispersion section to an operational position within the cylinder with the drive system; and then
   e) introducing product from the product inlet into the cylinder through the dispersion section with the plunger remaining in the cylinder.

2. The method of claim 1 wherein the step of the intrusive maintenance performed further comprises replacement of a screen connected to the plunger by at least a nut.

3. The method of claim 2 wherein the step of the replacement of the screen further comprises removing the nut located substantially at the center of the plunger.

4. The method of claim 2 wherein the step of replacement of the screen further comprises removing the distributor plate.

5. The method of claim 1 wherein the step of raising the plunger a predetermined distance further comprises raising the plunger at least six inches.

6. The method of claim 5 wherein the step of raising the plunger a predetermined distance further comprises raising the plunger about one foot.

7. The method of claim 1 further comprising the step of engaging a safety mechanism after raising the plunger, and disengaging the safety mechanism before lowering the plunger.

8. A method of accessing the interior of a chromatography column comprising the steps of:
   a) providing a chromatography column having a dispersion section with a product inlet, a cylinder connected to base in an operational mode, and a drive system;
   b) disconnecting the cylinder from the base;
   c) raising the cylinder a predetermined distance above the base with the drive system to a first maintenance position without the use of a crane;
   d) performing maintenance within the column; and
   e) lowering the plunger to the operational mode with the drive system returning the cylinder to the base;
   f) reconnecting the cylinder to the base; and then
   g) introducing liquid product through the product inlet into the cylinder with the plunger in the operational mode.

9. The method of claim 8 wherein the drive system is connected to a plunger in the operational and further comprising the step of raising the plunger with the cylinder during the step of raising the cylinder the predetermined distance.

10. The method of claim 8 wherein the step of performing maintenance further comprises removing a screen.

11. The method of claim 10 wherein the step of providing a chromatography column further comprises locating the screen at least partially between the cylinder and the base in the operational mode.

* * * * *